United States Patent [19]

Siegl

[11] 4,145,523
[45] Mar. 20, 1979

[54] ORGANOMETALLIC POLYMERS (A)

[75] Inventor: Walter O. Siegl, Dearborn, Mich.

[73] Assignee: Ford Motor Company, Dearborn, Mich.

[21] Appl. No.: 793,587

[22] Filed: May 4, 1977

[51] Int. Cl.² .................. C08G 83/00; C08G 79/00
[52] U.S. Cl. .............................. 528/395; 528/377; 528/423
[58] Field of Search ............... 260/2 M; 528/377, 395, 528/423

[56] References Cited

PUBLICATIONS

Journal of Organo Metallic Chemistry 107 (1976) C 27-30.

Macrocyclic Polymers, Packham et al., Polymer 10, 559, (1969).

*Primary Examiner*—John C. Bleutge
*Attorney, Agent, or Firm*—Edmund C. Ross, Jr.; Olin B. Johnson

[57] ABSTRACT

Organometallic polymers are made in liquid medium by contacting (A) bis-chelate ligands such as 1, 3, 5, 7-tetra (2-pyridylimino)-benzodipyrrole with (B) salts of divalent, hexacoordinate, transition metals such as nickel chloride. The organometallic polymers have high thermal stability and are suitable as colorants for organic materials including thermoplastic resins.

12 Claims, No Drawings

ORGANOMETALLIC POLYMERS (A)

This invention concerns organometallic polymers made by reacting (A) bis-chelate ligands and (B) divalent, hexacoordinate, transition metal salts. The bis-chelate ligand (A) can be represented as:

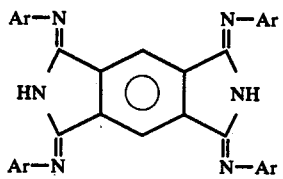

wherein Ar is:

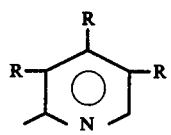

or

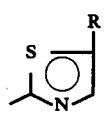

and each R is independently hydrogen, halo (e.g., chloro, bromo, or iodo) or an organic radical of up to about 100 or more carbon atoms. The organic radical can be hydrocarbon or substituted hydrocarbon (exemplary substituents being halo (e.g., chloro, bromo, or iodo), carboxy, hydroxy, mercapto, nitro, and the like). Examples of the organic radical include aliphatic, aromatic and mixed aliphatic-aromatic radicals, particularly those which have saturated or substantially saturated hydrocarbon groups ("saturated hydrocarbon" as used herein and in the appended claims includes aromatic hydrocarbons). Preferably, the organic radical is alkyl, aryl, alkaryl, aralkyl, alkaralkyl or the like, as well as any such radicals which are connected to the bis-chelate ligand (A) through connective moieties such as oxy, amino nitrogen, and thio, as, for example, alkoxy, aralkoxy and alkylthio. Examples of preferred organic radicals for R include alkyl and alkoxy up to about 25 carbon atoms, more preferably up to about 10 carbon atoms, e.g., lower alkyl and lower alkoxy. In preferred embodiments, all R's are hydrogen except one R which may be alkyl, alkoxy or halo, more preferably alkyl up to about 10 carbon atoms including straight and branched chain alkyl such as methyl, ethyl, isopropyl, s-butyl, t-butyl, heptyl and the like.

As the nature of R is not normally a critical aspect in the formation of the organometallic polymers, R can be chosen to vary, for example, organic solubility. For example, when Ar in I is (a), alkyl substitution at the 4 position to the ring nitrogen significantly increases solubility in the corresponding organometallic polymer.

The bis-chelate ligand (A) is conveniently made by reaction of 1,2,4,5-tetracyanobenzene with nitrogen-containing heterocyclic primary amines (e.g., 2-aminopyridine) in the presence of catalyst. Alkaline earth metal salts in alcohol (e.g., lower alkanols such as butanol) serve as catalysts. Particularly useful in this regard are alkaline earth metal halides such as calcium chloride.

Other preparative routes for bis-chelate ligand (A) are available and this invention is not limited by the route selected for their preparation. For example, other catalysts (e.g., nickel acetate) can be employed in the reaction of 1,2,4,5-tetracyanobenzene and nitrogen-containing heterocyclic primary amines.

Contact of bis-chelate ligand (A) with divalent, transition metal cation of (B) in liquid medium leads to the formation of the organometallic polymers. Importantly, the metal cation of (B) is one which can form hexacoordinate complexes. Examples of preferred metals include nickel, cobalt, zinc and cadmium.

The nature of the anion of the divalent, hexacoordinate, transition metal salt (B) is of comparative little importance and usually suitable anions include halide (e.g., chloride), carboxylate (e.g., acetate, valerate and stearate), sulfate or any other such anion which does not hinder contact of the bis-chelate ligand (A) and divalent, hexacoordinate, transition metal of (B) in the liquid reaction medium chosen. Mixtures of divalent, hexacoordinate, transition metal salts, both as to anion and/or cation mixtures (e.g., cobalt chloride or bromide and nickel chloride) may be suitably employed.

Polar medium which solvates both bis-chelate ligand (A) and divalent, hexacoordinate, transition metal salt (B) normally provides desired contact. Use of solvent pairs (e.g., lower alkanols and lower alkyl halides) is preferred for simultaneously dissolving reactants (A) and (B) and establishing desired contact.

As both bis-chelate ligand (A) and divalent, hexacoordinate, transition metal salt (B) will generally be solid at room temperature and pressures, the reaction to form the organometallic polymers of this invention can be conducted by addition of suitable liquid medium (e.g., cosolvents) to a dry mixture of (A) and (B). Alternatively, a solution of (A) can be admixed with a solution of (B) to form the polymers. Moreover, the reaction may also be conducted stepwise, as, for example, formation of a bimetal complex of (A), followed by further addition of (A) to the liquid medium.

The reaction to form the organometallic polymers may be conveniently conducted at room temperature up to about 50° C., but higher temperatures up to the decomposition of the product or reactants can also be employed.

When contacting bis-chelate ligand (A) and divalent, hexacoordinate, transition metal salt (B), maximum chain lengths are obtained at molar ratios of metal to ligand of 1:1. If the reaction is to be conducted in steps as by formation of a bimetal complex of (A) first, then a molar excess of metal is advantageously employed in the first step.

After the desired reaction is completed, the organometallic polymer can be separated from the liquid medium, if desired, by conventional techniques, as filtration and distillation. Acid formed can be removed by, for example, washing with water and/or with mildly basic aqueous solution, as, for example, aqueous ammonia solutions.

The organometallic polymer, formed of alternating bischelate (univalent, tridentate at each end) and divalent transition metal cation, is believed to correspond to the formula:

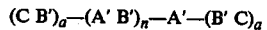   II wherein A' is a divalent bis-chelate corresponding to the formula I' below:

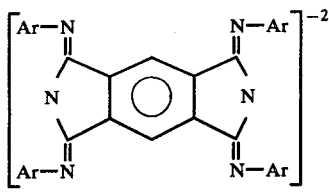

and Ar and R are as hereinbefore in Formula I; B' is a divalent, hexacoordinate, transition metal cation; C is an anion (e.g., chloride); a is zero or 1; and n is at least 2. Evidence of relatively short chain organometallic polymers is seen with gel permeation measurement methods, i.e., those wherein there are about 5 metal cations per organometallic chain, for at least a portion of the product of (A) and (B). In some instances, shorter chain materials, or even unreacted reactants may be left in the product of (A) and (B), as when the product is used as a colorant.

The configuration of the divalent bis-chelate A' is planar. Each side accordingly can function separately as a univalent tridentate ligand for a divalent, hexacoordinate, transition metal cation. Each succeeding bischelate on the polymer chain can coordinate to the preceding divalent transition metal cation perpendicular to the preceding bis-chelate A'. Schematically, this is represented by:

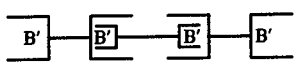

III wherein larger symbol

is one bis-chelate A' in a plane, and smaller symbol

is another bis-chelate A' which lies in a plane perpendicular to the preceding bis-chelate.

The organometallic polymers of this invention can have a large number of uses due to their unusual structural features and high thermal stability. Of interest, for example, are their yellow-orange colors making them suitable as dyes and pigments. Those organometallic polymers having higher organic solubility (e.g., when at least one R in each Ar at a 4-position to the ring nitrogen has 2 or more alkyl carbons, more desirably at least 4 alkyl carbon atoms) can be used to form yellow to orange tinctures with organic solvents. Moreover, the organometallic polymers are suitable to color thermoplastic resins, particularly in view of their high thermal stability. Thus, for example, the organometallic polymers may be dissolved and admixed in such resins as polyvinyl chloride to impart desirable yellow to orange coloration. Still further, the organometallic polymers, due to the conductive properties of the transition metal cations, are of interest in electrical applications.

The following examples are intended as illustrating this invention and not intended as limiting thereof. All parts are parts by weight and all temperatures are in degrees centigrade.

PREPARATION OF BIS-CHELATING LIGANDS

Example I

A round bottom flask is charged with 1 part 1,2,4,5-tetracyanobenzene, 3.96 parts 2-aminopyridine, 0.626 parts calcium chloride and 56 parts ethyl alcohol. The mixture is stirred for 10 days at 25° C.; then 67 parts 2-methoxyethanol is added and the ethanol is distilled off from the reaction mixture. The remaining yellow suspension is heated at reflux for 8 days. After cooling, the product is filtered and the residue washed with water/methanol and again with acetone. After drying, a greenish yellow powder is obtained which is crystallized from hot quinoline (MP 397°-9° C.). The greenish yellow powder contains the desired 1,3,5,7-tetra(2-pyridylimino)benzodipyrrole.

Example II

Following the general procedure of Example I, the bis-chelate ligands IIa–IIf are prepared from 1,2,4,5-tetracyanobenzene and the heterocyclic primary amines as follows:

| Compound | Primary Amine N-Heterocycle | Mp* |
|---|---|---|
| II a | 2-amino -4-methylpyridine | 340–1° C |
| II b | 2-amino -4-ethylpyridine | 353–5° C |
| II c | 2-amino -4-propylpyridine | 357–9° C |
| II d | 2-amino -4-butylpyridine | 435–7° C |
| II e | 2-amino -4-s-butylpyridine | 369–71° C |
| II f | 2-amino -4-n-amylpyridine | 317–8 ° C |

All ligands tested give confirmatory ir, nmr, and elemental analysis.

Example III

In this example, 2-aminothiazole

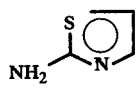

(4.21 parts) is used rather than 2-amino pyridine as in Example I. The desired bis-chelate ligand is recovered following the procedure of Example I.

Example IV

In this example, the procedure of Example I is followed except a mixture of 2-amino-4-methylpyridine and 2-amino-4-octadecylpyridine is employed rather than 2-aminopyridine. The desired mixed bis-chelate ligand is obtained.

Example V

A flask is charged with 1 part bis-chelate ligand II e, 3.4 parts nickel acetate, and 27 parts methanol. The mixture is stirred for two days at 24° C., then filtered. The residue is washed with water and methanol and then dried. The nickel acetate complex of II e is obtained.

PREPARATION OF ORGANOMETALLIC POLYMERS

Example A

A flask is charged with 1 part bis-chelate ligand IIe 0.42 parts nickel acetate, 24 parts chloroform; and 4.2 parts methanol. The dark red reaction mixture is stirred at 24° C. for 24 hours. The solvent is distilled from the reaction mixture and the residue is washed with ammonium hydroxide and with water. After drying, a rust colored solid is obtained which is the organometallic polymer.

Example B

The procedure of Example A is followed except nickel chloride (0.40 parts) is used rather than nickel acetate. A solid rust colored polymer product is obtained.

Example C

The procedure of Example A is followed except cobalt acetate (0.42 parts) is used rather than nickel acetate. The corresponding cobalt polymer is obtained as a rust colored solid.

Example D

The procedure of Example A is followed except nickel acetate (0.21 parts) and cobalt acetate (0.21 parts) is used rather than nickel acetate alone. The mixed metal polymer is obtained as a rust colored solid.

Example E

The procedure of Example A is followed except the bis-chelate ligand II b replaces bis-chelate ligand II e on an equal molar basis. The nickel polymer of II b is obtained as a rust colored solid.

Example F

The procedure of Example A is followed except that a mixture of bis-chelate ligands II e (0.5 parts) and II b (0.42 parts) is used rather than the bis-chelate ligand II e alone. The desired mixed ligand polymer is obtained as a rust colored solid.

Example G

A flask is charged with 1 part bis-chelate ligand II e, 1.3 parts of the bimetal nickel acetate complex of II e (prepared in Example V), 24 parts chloroform, and 4.2 parts methanol. The mixture is stirred at 24° C. for 24 hours. The solvent is removed by distillation and the residue is washed with ammonium hydroxide. After drying a solid rust colored polymer is obtained.

Example H

The procedure of Example G is followed except that a mixture of nickel acetate complex of II e (0.65 parts) and the cobalt acetate complex of II e (0.65 parts) is used rather than the nickel acetate complex alone. The solid mixed metal polymer is obtained.

Example I

The procedure of Example G is followed except that the nickel acetate complex of bis-chelate ligand II b (1.15 parts) is used rather than the nickel acetate complex of bis-chelate ligand II e. The solid rust colored mixed ligand polymer is obtained.

Other organometallic polymers using the bis-chelate ligands of Example II can be made following the above procedures. Also, zinc and cadmium salts (e.g., zinc or cadmium chloride) can be employed in place of the nickel or cobalt salts used in the above examples.

Example 1

A dye solution is formed of 1 part by weight rust colored solid of Example A and 390 parts by weight of tetrahydrofuran (THF).

(a) The dye solution is added to a solution of polyvinylchloride resin (Stouffer Chemical ACFX-97132) in THF so that the resultant film cast (pale yellow) comprises 1 part by weight of the dye and 2370 parts by weight of the resin.

(b) Following the procedure of (a), a yellow-orange film is cast comprising 1 part by weight dye and 89 parts by weight of the same polyvinylchloride resin.

(c) Following the procedure of (a), an orange film is cast comprising 1 part by weight dye and 15 parts by weight of the same polyvinylchloride resin.

Example 2

The procedure of Example 1 is followed except the films are cast with the rust colored solid of Example B acting as the dye. Films are cast with colorations similar to those of Example 1 at comparable concentrations.

What is claimed is:

1. A method for preparing organometallic polymers of alternatively perpendicular bis-chelates which comprises (1) contacting in liquid medium bis-chelate ligand (A) corresponding to the formula

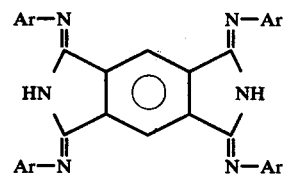

wherein Ar is:

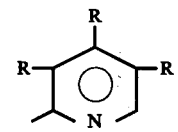

or

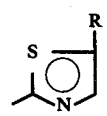

and each R independently is hydrogen, halogen or an organic radical of up to about 100 carbon atoms with divalent, hexacoordinate, transition metal salt (B), and (2), optionally thereafter contacting additional bis-chelate ligand (A) with the product obtained in (1).

2. The method according to claim 1, wherein Ar is (a) and each R is independently hydrogen or hydrocarbon.

3. The method according to claim 2, wherein the metal salt (B) comprises nickel, cobalt, zinc, cadmium or mixtures thereof.

4. The method according to claim 3, wherein the metal salt (B) comprises nickel or cobalt or mixtures thereof.

5. The method according to claim 4, wherein the liquid medium comprises a polar medium which solvates bischelate ligand (A) and the salt (B).

6. A method according to claim 5, wherein in step (1) the bis-chelate ligand (A) is contacted with the metal of (B) in a molar ratio of about 1:1.

7. An organometallic polymer made according to claim 1.

8. An organometallic polymer made according to claim 2.

9. An organometallic polymer made according to claim 3.

10. An organometallic polymer made according to claim 4.

11. An organometallic polymer made according to claim 5.

12. An organometallic polymer made according to claim 6.

* * * * *